(12) United States Patent
Muller

(10) Patent No.: US 10,623,696 B1
(45) Date of Patent: Apr. 14, 2020

(54) COMMUNICATION SYSTEM FOR USE WITH PROTECTED PERSONS

(71) Applicant: Paula Muller, Keyport, NJ (US)

(72) Inventor: Paula Muller, Keyport, NJ (US)

( * ) Notice: Subject to any disclaimer, the term of this patent is extended or adjusted under 35 U.S.C. 154(b) by 0 days.

(21) Appl. No.: 16/532,648

(22) Filed: Aug. 6, 2019

Related U.S. Application Data

(60) Provisional application No. 62/714,810, filed on Aug. 6, 2018.

(51) Int. Cl.
*H04N 7/14* (2006.01)
*G06F 21/30* (2013.01)
*G16H 80/00* (2018.01)

(52) U.S. Cl.
CPC ........... *H04N 7/142* (2013.01); *G06F 21/305* (2013.01); *G16H 80/00* (2018.01)

(58) Field of Classification Search
CPC ....................................................... H04N 7/14
See application file for complete search history.

(56) References Cited

U.S. PATENT DOCUMENTS

| | | | | |
|---|---|---|---|---|
| 9,270,940 B1* | 2/2016 | Aravkin | .................. | H04N 7/147 |
| 2006/0178173 A1* | 8/2006 | Miller | .................. | H04M 1/663 |
| | | | | 455/575.1 |
| 2006/0276232 A1* | 12/2006 | Engevold | .......... | H04M 1/72588 |
| | | | | 455/564 |
| 2010/0069087 A1* | 3/2010 | Chow | .................. | G08B 21/023 |
| | | | | 455/456.1 |
| 2010/0112986 A1* | 5/2010 | Ellingham | ............ | H04M 1/663 |
| | | | | 455/414.1 |
| 2010/0250985 A1* | 9/2010 | Gupta | .................... | G06F 1/3203 |
| | | | | 713/323 |
| 2013/0178151 A1* | 7/2013 | Itzhaki | .............. | H04W 52/0245 |
| | | | | 455/26.1 |

* cited by examiner

*Primary Examiner* — Olisa Anwah
(74) *Attorney, Agent, or Firm* — Graham Casanova Alig; Alig Patent Law

(57) ABSTRACT

A method including a dedicated device for simple, automatic, and immediate communication system for protected persons, who may for short or long term benefit from assistance, with oversight by an administrator, who manages which persons are trusted to communicate with the protected person through the system. In particular, the present invention focuses on pervasive presence, the system does not go to sleep, continually monitoring and measuring objective and subjective aspects of the protected person's experiences, states, and system states, including health and communication measures, maintains a schedule with reminders, and a series of adaptive prompts, for example, medications and appointments, social activities and engagements, and automatically and in a simple manner, connects the protected person with trusted persons and authorized services and features through an adaptive customizable interface, by a variety of means such as touch, audio and visual. It connects through gateways to many services and content, with accommodation for vision, hearing, mobility, language, and other needs, thus reducing cognitive burden and stress for the protected person while maintaining ease of use and important social connections to promote emotional well-being.

13 Claims, 11 Drawing Sheets

Protected Person

COMMUNICATION SYSTEM FOR USE WITH PROTECTED PERSONS

CROSS-REFERENCE TO RELATED APPLICATIONS

This application claims priority Provisional Patent Application 62/714,810 filed on Aug. 6, 2018, which is hereby incorporated by reference in its entirety.

FIELD OF INVENTION

This present disclosure relates to methods and devices for communication, particularly the disclosure relates to secure communication. More particularly the disclosure relates to methods and devices for secure communication wherein the communication may involve one person who is under guardianship of another person.

BACKGROUND OF THE INVENTION

People are increasingly relying upon technology to stay connected with loved ones, their peers, healthcare providers, etc. With systems such as email, text messages, video conferencing, and new media becoming mainstream, formerly conventional methods of correspondence are being used less frequently. This is in part because technology allows us to connect more quickly and share more information than customary methods. For example, using technology we can send pictures, audio files, and even video conference with people at the touch of a button. Even medical or service providers and benefits may be managed primarily online. In addition, these systems are becoming less and less expensive and, in many cases, let us connect for less than the price of a postage stamp. Moreover, society is becoming more mobile, at times living at a distance or engaged in work or other activities for long periods of time and reducing access to loved ones.

Unfortunately, not everyone is able to benefit from these technologies. In particular, elderly, those with disabling conditions, children, and others are often unable to realize technology's potential because of the learning curve associated with these systems. Either because of medication, neurological conditions or natural aging process, the neural connections or other biological systems that process and retain new information begin to change or deteriorate, making it more difficult to learn how to use new devices. Because the technological devices require learning new and different systems, special populations, those under stress, people with medical conditions, and others including the elderly may struggle to incorporate these devices and all their extended benefits into their lives. The barriers to incorporate these benefits may result in anxiety, depression, stress, overwhelming the person's ability to learn, paradoxically creating an undesired emotional experience. The person may not perceive the usefulness of the engagement with technology, or they might not be involved in a social or workplace setting whereas a group technology learning takes place. The effect of this is elderly or special populations often feel left behind and isolated from the rest of the world, often with nobody to turn to in order to bridge the gap. Their family members may live at a distance or may be busy, their partner, mate or friends may be infirmed or gone, or have moved away, they may speak a language not shared by those nearby. This experience compounds the situation and the natural process of aging that may inhibit mobility, senses including hearing and vision, cognitive, and or other elements of health and well-being, and or become a challenge to independence. Sometimes these experiences are temporary during illness or adjustment. Sometimes they can occur when an individual has a challenging emotional experience, and they may withdraw. Or they might have special communications needs for a variety of other reasons. They may become socially and or physically isolated. For some it may compound existing conditions, for others, it may result in new problems.

As reported by several studies, isolation can have severe negative health consequences. Isolation and loneliness are major risks for depression and have been linked to severe long-term illnesses. With this, integration and social engagement of the elderly and special populations are critical for their health, well-being and quality of life. It is desired to have a method of communication between an individual that may require oversight or protection (protected person) and another person in a trusted environment (communication with trusted people) that is approved by an administrator and is instant, secure, always available and effortlessly.

Patent Application Publication 20140359453 to Mark Palfreeman published on Dec. 4, 2014 entitled, "Systems and Methods for Displaying Images on Electronic Picture Frames" discloses a computer-implemented method for displaying images. It comprises collecting a plurality of images from one or more image repositories and generating a slideshow of images for display on an electronic picture frame. Whereas previous systems for displaying pictures in frames may be automatically updated, may be robust through power outages and the like, and may be adaptable to the user's preferences, the present invention may be updated to meet new functionality through a server. Therefore, novel services and features, not just updated versions of the picture frame, will be enabled by the current invention. Not only can the present invention display pictures and other features to the user's preferences, it can also customize the presentation and features to meet the needs of the user through several methods of the present invention. The administrative person can configure the interface features to meet the sensory, cognitive, or preferences of the protected person. Also, specialists who understand how protected persons with health, language, communication, dementia, cognitive issues, or sensory impairments such as vision or hearing issues may benefit from specific configurations of features and interface presentations can modify the system to simplify interactions and improve the usefulness of the experience for the protected person. The present invention can be modified to accommodate multiple types of input and display necessary for interactions by protected persons, administrative persons, and or trusted persons.

Chinese patent CN201131117Y published on Oct. 8, 2008, discloses an electronic device for the elderly aimed at solving cultural problems of an aging population wherein the family may have more elderly members than the younger generations. Across the globe many societies are facing challenges as families are often no longer living near one another; and when acute or chronic conditions impact a person's abilities to manage independently, there are efforts to address the situation with technology. In China, as showcased by patent CN201131117Y for example, a solution is provided for monitoring the elder, whose family members are migrant workers. The system monitors blood pressure, temperature, and other vital signs and reads e-books aloud using speech technology to reduce complexity for seniors with low vision, provides a simplified user interface, and enables emergency calling features. However, the system does not provide for pervasive presence, customized interface, and simple immediate access for the elder to the family member at a distance, in particular, in response to a trigger, or a simplified request by the protected person. With the present invention, the user interface is adapted to the needs of the user and the task at hand to reduce cognitive load. The present invention provides for the pervasive presence to monitor and then take action based on settings selected by the administrator, and close the loop of social contacts based on a number of conditions that may be satisfied in the script of actions. The present invention is also ideally designed to manage updates to all and any features and functions over time. While the system provides a gateway to service providers, the administrator can block access to the wider internet content to reduce risks and complexity for the protected person. In addition, the present invention simplifies and pre-schedules and provides triggers for many social interactions to reduce likelihood of loneliness, isolation, and anxiety which might occur in the life of a person with an acute or chronic medical condition, or who is aging, or finds themselves to be in a changed social situation; and can assist when a person who has been prescribed medication for a condition, has challenges managing to maintain orientation to the activities, places and things in their lives, and the connections with their family, friends, or peers.

US Patent Publication 2016/0098759 to Andre et al. published on Apr. 20, 2006, entitled, "System And Method For Enabling Efficient Digital Marketing On Portable Wireless Devices For Parties With Low Capabilities," discloses a system and method provided for managing digital marketing to a multiplicity of consumers by way of portable wireless digital devices. This and other types of technology provide methods of presenting information to elderly in an easier way and provides access to other online features and services in the manner used by the general population. Whereas, the present invention provides secure access, adaptive interfaces, and restricts wide access, thereby providing protection from complexity, predatory sites, and other circumstances as deemed appropriate by the administrator. In addition, the present invention provides for simplified means and methods to customize the interface to meet the special requirements of the individual, in particular, given the task flow, the abilities of the protected person, goals of the services being provided, and including and considering objective and subjective measures gathered during interactions and use of the device, sensor information, plan, etc. In addition, the present invention provides for a pervasive presence and companion to the individual, even when the administrator and trusted people are unavailable. The present invention maintains an engaging dialogue and connection with the protected person including schedules, upcoming events, pictures of familiar people, places, and things, etc. as well as programming.

U.S. Pat. No. 9,020,476 issued on Apr. 28, 2015 to Leipez et al. entitled "System and method for remote care and monitoring using a mobile device," discloses a system and method for remote care and monitoring of the user of a mobile device. Whereas other systems, such as the system described in U.S. Pat. No. 9,020,476, provide for monitoring elders for events and alerts, and provide for one-click dialing in the event of emergencies, and they provide for automatic dialing in certain conditions, for example, a sensor detecting a fall, these systems do not provide flexible interface options for those with limited abilities, language, cognitive challenges, sensory, emotional, and other issues. In addition, they fail to provide for pervasive companion to promote simple social engagement. The present invention provides for dialog that maintains a diverse and more holistic record of prompts including social interactions and responses from the protected person as well as objective measures as a means to determine the condition and status of the protected person. Status trends indicate the likelihood of events happening in the future, services and features needed, indicators of depression and or anxiety, health, wellness, and quality of life.

The Patent Application Publication 20140359453 to Mark Palfreeman published on Dec. 4, 2014, the US Patent Publication 2016/0098759 to Andre et al published on Apr. 20, 2006, and the U.S. Pat. No. 9,020,476 issued on Apr. 28, 2015 to Leipez et al. are each hereby incorporated by reference in their entireties.

SUMMARY OF THE INVENTION

Herein is presented a method of communication between persons which comprises communication between at least two entities. In the conduction of this communication there is a first person, one or more second persons and one or more third persons. The actual communication occurs between the first person and one third person. More than one third person can participate in the communication. Each person involved in the conduction of this communication has a unique identity. The second persons and the third persons are distinct from the first person. However, the identity of the second person can be the same identity of the third person. Before communication can proceed with a minimum of one second person must know the identity of the third person and have granted approval for that third person to participate in communicating with the first person. The communication is conducted by a first device that is coupled to a second device by electronic means; wherein the first device is in the presence of the first person and the second device is in the presence of the third person. Furthermore, the first device is always active when it is in the presence of the first person.

The communication can be vocal. In this embodiment, the device is equipped with a microphone capable of transducing sound and a speaker capable of transmitting sound. The communication can be visual. In this embodiment, the device is equipped with a camera capable of transducing images and a display capable of displaying transmitted images. The communication can involve touch. In this embodiment, the device is equipped with touch-sensitive display capable of displaying images and transducing touch.

The first person of the above embodiment can be a child. The first person of the above embodiment can also be a person over the age of 65. The first person of the above embodiment can be a person who has been legally determined to incompetent. The first person of the above embodiment can be a person who has been medically determined to have diminished mental functions.

In another preferred embodiment, the device is configured to recognize a PIN as a code by which the second person can grant approval for a third person to communicate with the first person. In a particularly preferred embodiment, the third person communicates a PIN to the device to confirm the third person has granted approval for communication with the first person.

DETAILED DESCRIPTION OF THE INVENTION

Herein is presented a method of communication between persons which comprises communication between at least two entities.

Figure 1:
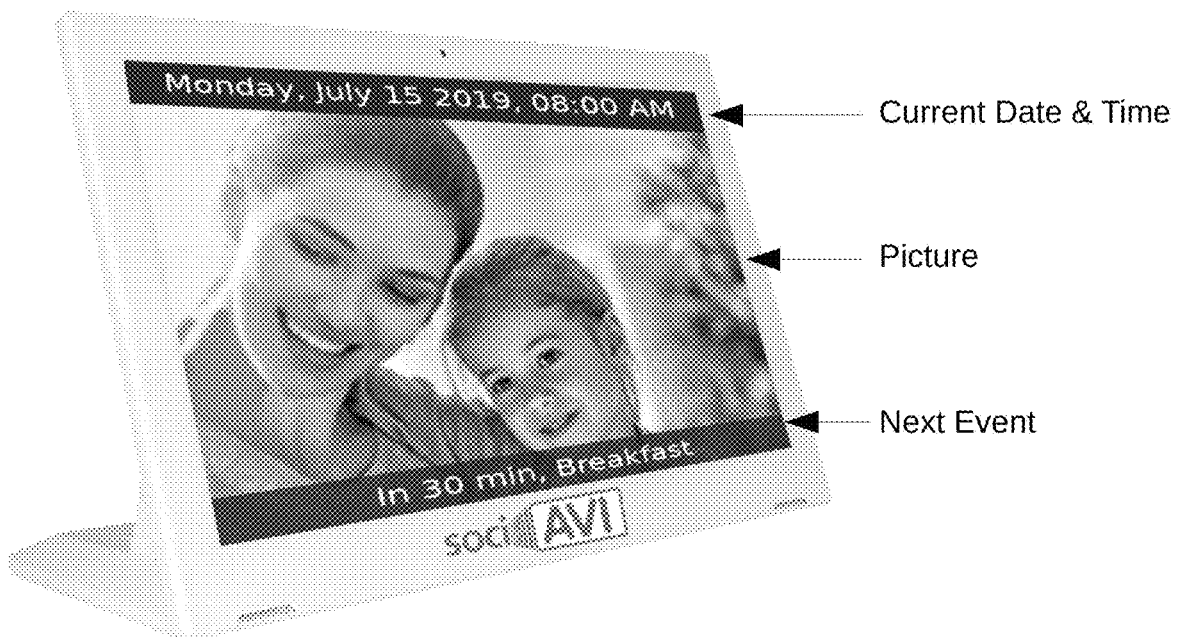
FIG. 1 is an illustration of the device showing a typical main screen of the program as seen from the perspective of the protected person.

The device can be useful when not being actively used for communication. FIG. 1 shows a representative image of the device configured in a main screen. Here the device displays information that is both instructive to the protected person and informational that stimulates an emotional response. In FIG. 1 as a representative example, a daughter and granddaughter are presented.

Figure 2:
FIG. 2 is an illustration of the device showing a typical scheduling screen of the program as seen from the perspective of the protected person.

Similarly as an illustrative example, FIG. 2 depicts the device configured to display useful information to the protected person, such as a reminder of their name, the local weather, time of day, etc. FIG. 2 also shows that the device can be configured to encourage interaction when the protected person is capable of such interaction. In this illustrative example the device is enticing the protected person to start a video.

Figure 3:
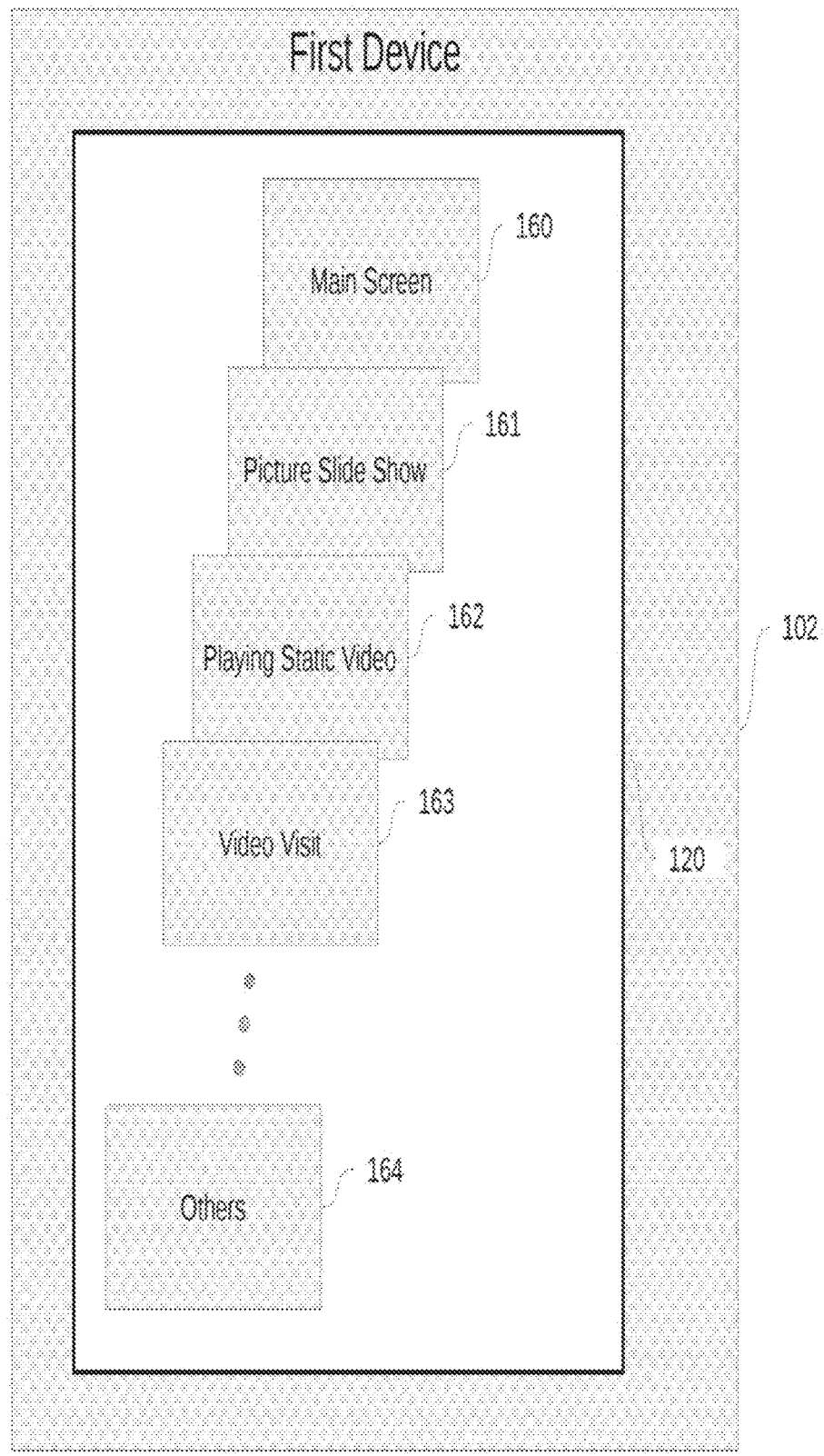
FIG. 3 is a schematic of the functions of the device as they might be presented to a protected person.

FIG. 3 shows a schematic of how the device could be configured to present layers of information. The default screen is the Main Screen 160 with the calendar, weather and time. The Picture Slide Show 161 is presented on top of it, and it appears when the device is inactive. When a video comes a new overlay appears on top like Playing Static Video 162, or a Video Visit 163 and subsequently, any new feature would appear as a new overlay 163 that is presented automatically or by the touch of a visible button or a voice-activated command. There is no use of pinch, zoom, scroll or swipe, or use of menus to navigate or use of keyboard.

Figure 4:
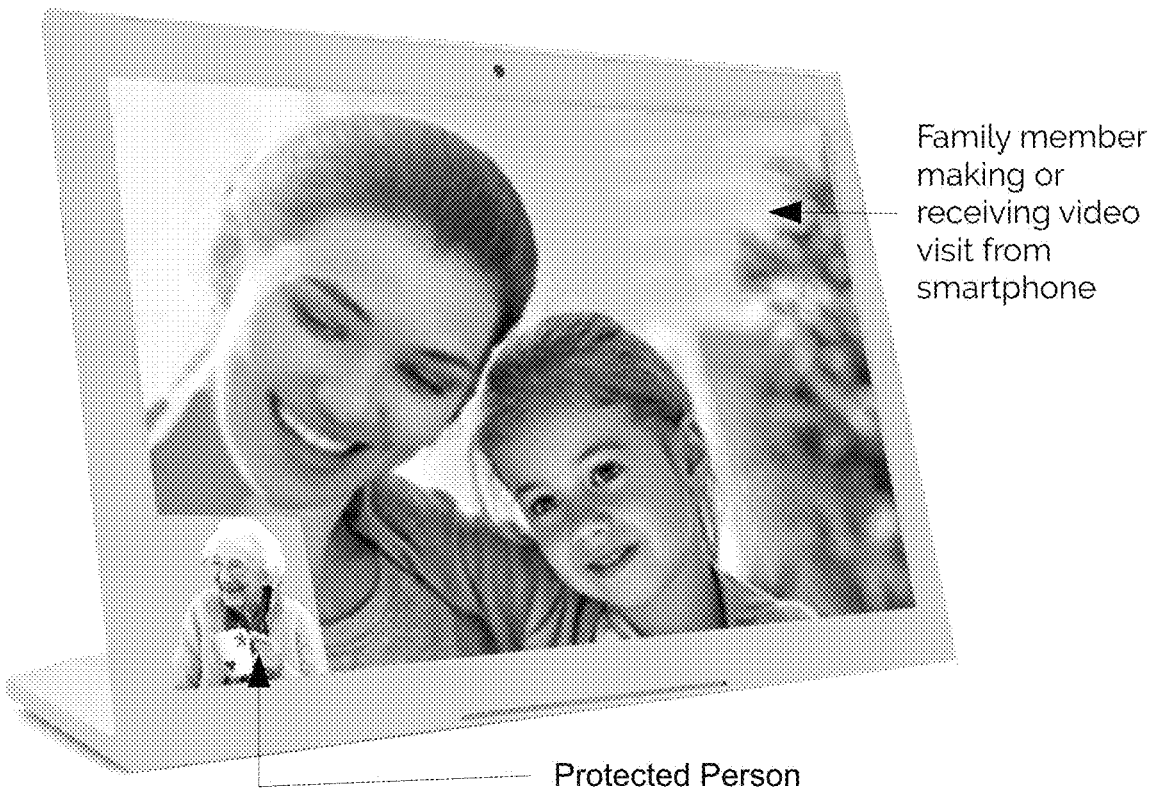
FIG. 4 is an illustration of the device showing a typical communication screen of the program as seen from the perspective of the protected person.

FIG. 4 illustrates the status of device when it is being used for communication. In the instance depicted by FIG. 4 a video call between the protected person and their daughter and granddaughter is taking place. In the conduction of this communication, there is a protected person (a mother as depicted in FIG. 4), one or more trusted persons (two trusted people: a daughter and granddaughter depicted in FIG. 4) and one or more administrators (the daughter in the example of FIG. 4 not depicted). The actual communication occurs between the protected person and one or more trusted persons. More than one trusted person can participate in the communication, as shown in FIG. 4. Each person involved in the conduction of this communication has a unique identity. The trusted persons and the administrators are distinct from the first person. However, the identity of a trusted person can be the same identity of the administrator: one person can be both a trusted person and an administrator at the same time. For instance, the daughter is both a trusted person and an administrator in the example depicted in FIG. 4.

Figure 5:
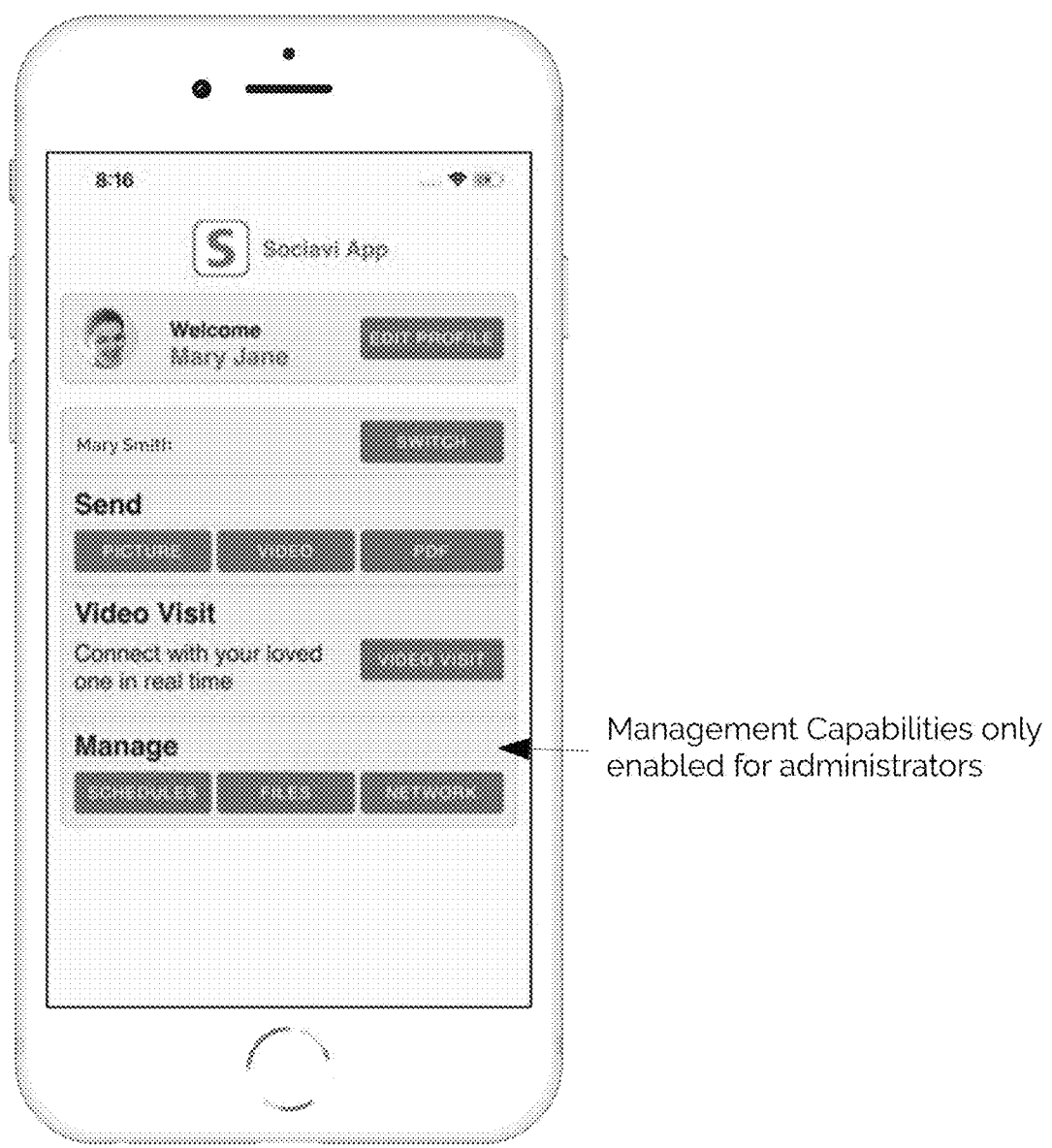
FIG. 5 is an illustration of the device showing a typical main screen of the program as seen from the perspective of the administrative person.
Figure 6:
FIG. 6 is an illustration of the device showing a typical communication screen of the program as seen from the perspective of the trusted person.

Before communication can proceed, a minimum of one administrator must know the identity of the trusted person and must have granted approval for that trusted person to participate in communicating with the protected person. In the example depicted in FIG. 4, the daughter approved both the granddaughter and herself as trusted persons (see FIG. 5). The communication is conducted by a first device (the device of FIG. 4) that is coupled by electronic means to a second device (the device depicted in FIG. 6). The first device is in the presence of the protected person and the second device is in the presence of the trusted person. Furthermore, the first device is always active when it is in the presence of the protected person, see Pervasive Presence.

Figure 7:
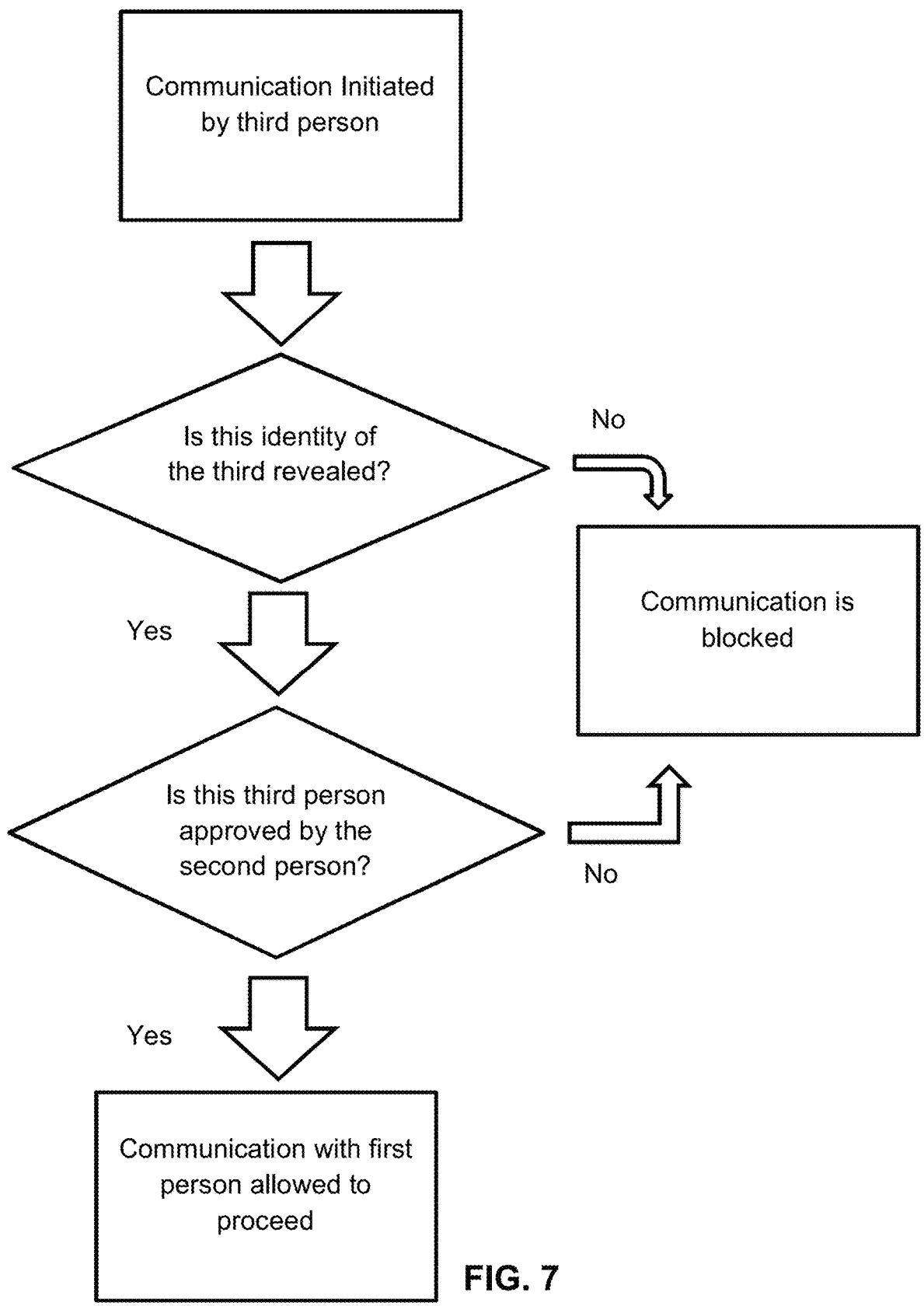
FIG. 7 is a flow chart showing the steps conducted when a person is attempting to communicate with the protected person.

FIG. 7 depicts a flow chart which shows the process for verifying that a potential communicator is, in fact, a trusted person. Communication is attempted. In order to verify the communicator is a trusted person, the identity of the communicator ought to be revealed. This is the first decision of the flowchart of FIG. 7. If the identity is blocked the call is blocked. If the identity if known the second decision is to determine if a second person or administrator has approved the communicator as a trusted person. If the communicator is confirmed as a trusted person the communication proceeds. If the communicator is not confirmed as a trusted person the communication is blocked.

Figure 8:
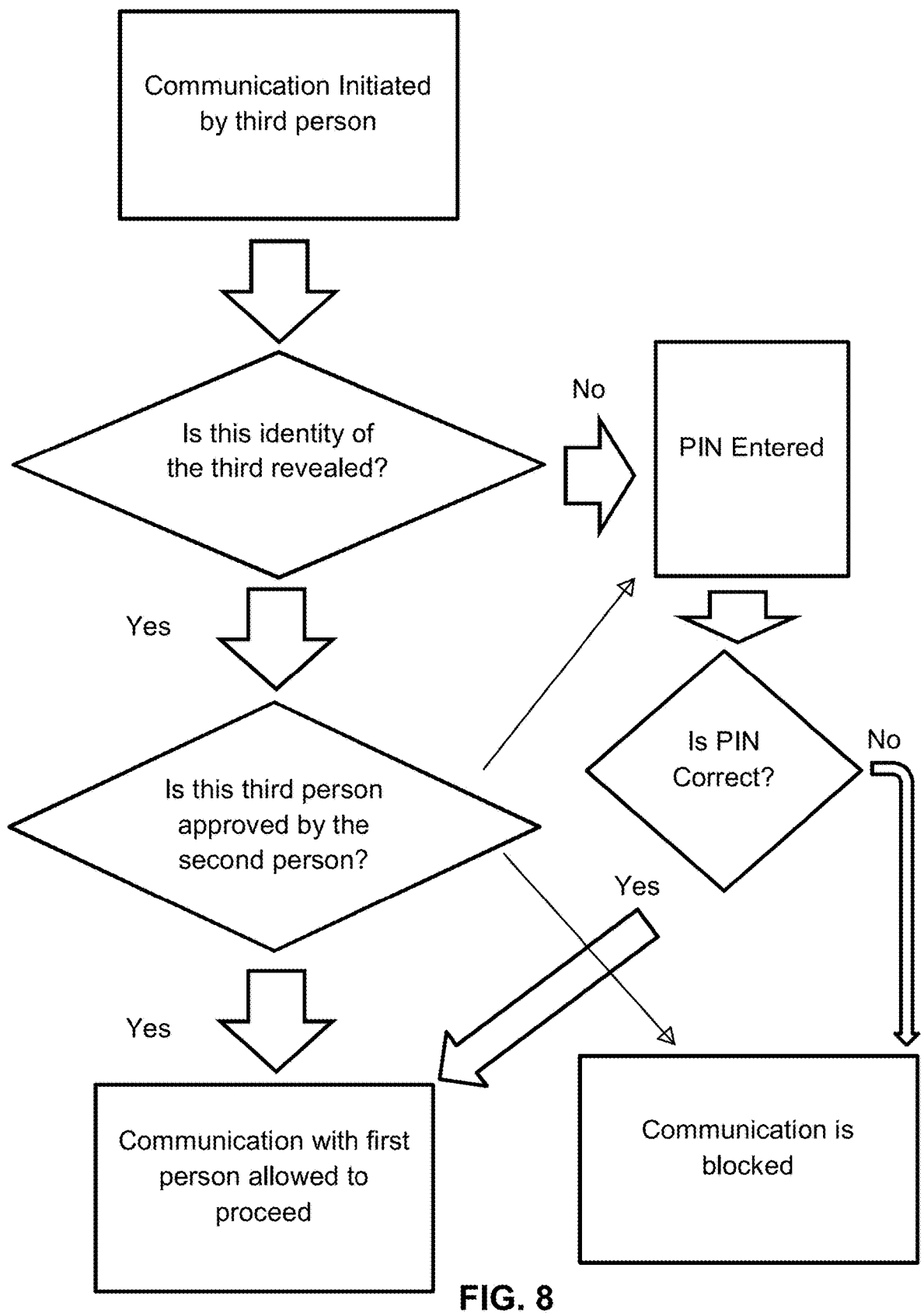
FIG. 8 is a flow chart showing the steps conducted when a person is attempting to communicate with the protected person and is using a PIN to demonstrate trustworthiness.

Depicted in FIG. 8 it is another embodiment of the invention where a PIN confirms the person is a trusted person. The device is configured to recognize a PIN as a code by which the second person can grant approval for a third person to communicate with the first person. In a this embodiment, the third person communicates a PIN to the device to confirm the third person has granted approval for communication with the first person.

Dedicated Device

The dedicated device, pervasive presence, and its adaptive features and functions become a safe and secure emotional companion device for the protected person, with oversight by the administrator. The protected person can rely on an ongoing and continued dialogue with the dedicated device in an easy and automatic way, because the device does not go to sleep. The dedicated device presents a view on screen or by alternative means and methods of the state of the protected person, and options that are available to the protected person, for example, an adapted interface might provide pictures of the loved ones for the protected person to touch to initiate communications, through video visits, or by sending a message, for example, provides a safe gateway to other features and services, and for other purposes. The dedicated device presents the emotional and health state of the protected person, and solicits engagement by the protected person, as a companion would, provides helpful information, simplified access to communication, reminders, schedules, healthcare monitoring and management, and is updated automatically without intervention by the protected person. The dedicated device is a method to manage communication, monitor, articulate, and verify the protected person's state, and adapt or promote actions to improve emotional valence and social interaction, to reduce isolation, stress, and loneliness, to reduce complexity, and for the best health outcomes.

Second Device

This is a generic device that provides access to trusted person or persons, and it may be used by the administrator to manage features, functions, access, interface, and oversight of the protected person. The second device is used by the administrator to establish or to check settings, to review statistics, to order and review reports, and more. The second device, learning, and features of the server together provide methods to configure and render the interface for the protected person to conduct a variety of tasks that are made accessible through the dedicated device.

Configurable Interface

For protected persons, a configurable interface adapts in consideration of measurable objective and subjective skills, aspects of memory and concentration, mobility, time of day, medications, and other aspects that impact the protected person's ability to interact with the dedicated device, and perform any and all of the functions required, desired, etc. The state of the protected person is assessed and monitored, the state of the system is monitored, the schedule and tasks are compared with the basic and range of skills of the protected person. An important aspect of the present invention is to be able to easily and conveniently be able to provide for appropriate interface designs for many protected persons; methods of the present invention include analysis of each task to be conducted by the users. Once the task has been documented and the system functions and features are made available, then these system functions are configured to optimize the skills of the individuals who will use the system to complete the tasks. For example, a protected person might have difficulty locating a contacts list, scrolling through, or searching by name, and finding the number of her daughter. Therefore, in the configuration of the interface for this protected person, a picture of the daughter's face might be an ideal means to present the number for the protected person who only has to touch the face of her daughter to connect a video visit. Therefore, the task flow adapted to the abilities of the protected person, and a means of monitoring success is an important aspect of the present invention. Since these abilities may vary over time, it is crucial to track them as they evolve in order to anticipate and recommend appropriate interface strategies for that protected person. For example, for some persons, there are times when they may be very capable of reading from a screen and recognizing their family members' names and faces; yet later in the day, or when the medications are particularly overwhelming, the same person may have difficulty with memory, orientation, and identification of the people, places, and things they ordinarily enjoy. The adaptive interface is able to detect these variables and recommend interface options that will meet the changing requirements of the individual. The dedicated device and pervasive presence detects abilities and changes in the abilities of the protected person, and offers a new configuration for the interface involving alternative input and display methods to meet the needs of that protected person at that particular state, and for that specific system state. These configurations can be short or long term, or they can be identified as no longer serving the needs of the protected person by observing statistics and determining the protected person is not responding, engaging, or another measure is being missed. In that case, a new assessment can be conducted for a new configuration to be established. A significant aspect of the invention and in particular, the configurable interface, provides for a collection of age progression images of people known to the protected person. If the protected person does not recognize her daughter from a recent photograph, but instead recognizes a photograph from childhood, then a sequence of photographs can be presented, with additional media and memories, to create an orientation for the protected person to reduce anxiety, and extend the social connectedness to loved ones. In this manner and in other ways, the present invention can be easily used with its Configurable Interface to display individual media or sequences, whether images, videos, sound files, textural, links to webcams of loved places, artwork, or other, that maintain important social connections and orientation to people, places, and things that are relevant to the protected person.

Adaptive Features

For a protected person, one might anticipate that variables measured by the system and the pervasive presence will not remain constant. Therefore, it is an important aspect of the present invention to monitor the protected person, the environment, social interactions, and other important measures to determine for example, the state of the protected person, the prescribed and scheduled activities and features of the system, and infer and or determine health, emotional valence, performance in Activities of Daily Living, Instrumental Activities of Daily Living, and more. The pervasive presence might, for example, use heart rate to conduct an analysis to determine heart rate variability, and from that measure, determine emotional condition. Alternatively, the system might use pressure sensors in the furniture to determine how sedentary the protected person has been and if there is a trend. The system might also use cameras, or gyroscopes to measure exercise and rehabilitation compliance, for example, and determine the state of the protected person. An important aspect of the invention, the Adaptive Features, use measures from the system to determine or infer the states of interest, then recommend a new action. For example, when the Pervasive Presence determines that the protected person has not left the sofa for three hours, and the heart rate variability has determined there is an emotional valence indicating sadness or stress, then the system can select from a library of features an appropriate action to take to reach the individual on the sofa, and engage that person in activities, or social dialog. An important aspect of the invention involves the Pervasive Presence determining that the protected person is still lingering in the bed well into the morning. Emotional valence measures are indicating stress and sadness. Upon looking back at other measures, the Pervasive Presence determines that this protected person who suffers from Asthma, is having a very difficult time sleeping. Lack of sleep can lead to symptoms of depression and dementia. The system of this invention will send messages and recommendations to administrators, healthcare providers, and adapt to engage the protected person in sleep assistance, wake notifications and assistance, appropriate levels and types of exercise, additional emotional support features such as social interactions, and appropriate media.

The pervasive presence monitors complex activities, and adapts to the changes taking place in the state of the protected person. Depending on the progression of these abilities, the system can also recommend appropriate adaptation to support the protected person in these activities, providing dignity, and through increased support, the system is reducing stress and anxiety. The present invention is particularly helpful to protected persons living in the community, because of these adaptive features. One is expected to be performing a few more independent activities of daily living when in the community. They may be complex, and memory can fail. But giving up on these joyful experiences can be isolating and depressing. Therefore, the adaptive features of the present invention can be used to create monitors and reminders of those cherished activities, such as caring for a pet, shopping and obtaining medications, learning safety procedures, managing money, maintenance, managing communication, scheduling important activities, and more. The adaptive interface can identify when the administrator will be needed for exception conditions, for example.

Accessibility Features

The invention is a system for real-time, instant, scheduled, practical, and very simple communication for the protected individuals or group of protected individuals, for example, the elderly, those with disabling conditions, the infirmed, students, children, residents of a community or members of an organization, those in rehabilitation, and others. Managed through a dedicated device, the protected individuals can stay connected and engaged with their loved ones, providers, and community without having to struggle with cumbersome issues that often occur with technology, and or without risking security, and or providing supervision, monitoring, and surveillances, and while also maintaining appropriate levels of independence, dignity, and privacy.

One embodiment of the invention is a dedicated device that is configurable, interoperable, connected, access point, links to sensors and actuators, and the like. Such a device features a touch screen with at least one front-facing camera, speakers, microphone, connectivity, internet access. In one embodiment of the invention, the size is configured to assure visibility for the protected individuals. In this embodiment, the display is more readily readable for text and more appreciated for images than a typical smartphone hand-held device and not as unwieldy as a tablet device for a protected person with limited vision. The invention is adaptable to the needs of the protected individuals, or group of protected individuals, with regard to visibility, audibility, special interface devices, actuators, sensors, etc. The dedicated devices are configured with a suitable operating system capable of installing and running the application that allows the protected individuals to communicate. The dedicated device is connected to a communication network provides a pervasive presence. The dedicated device can be configured to be always standing by and or active, with controllable and varying levels of monitoring, assessment, security, and privacy. Various accessories may be connected easily to the dedicated device. For example, such accessories can be configured to accommodate special needs. Such needs include but are not limited to, straw input, gesture recognition system, eye tracker, pressure mats, and others. In addition, a variety of resources may be connected including sensors, monitors, actuators, robots, and other devices.

The ideal embodiment provides a means to update and control the dedicated device on behalf of a protected individual or group of protected individuals, locally or remotely, in real time, on a schedule, as needed, by a trusted agent, professional, and or service provider, and that means to update may be enabled through a list of enabled authorized agents, and may also be enabled through a PIN or password. The trusted agent can engage in a virtual visit to the location of the protected individual through a pervasive system, by camera, microphone, logs, sensors, in real time and by review, also see the presentation experienced by the protected individual or group, in real time or in review, and drive the system, and or create an experience to be delivered to the individual or group at a set time, by schedule, or on demand.

The ideal embodiment provides a pervasive presence and manages transactions involving remotely controlling or updating software and features on behalf of the protected individual or group of protected individuals and therefore security is an important part of the system provided through premise software and features, the network server, devices, and methods.

Communication

The devices and methods described herein assist and/or allow for communication between two or more people, wherein one person is a protected person. Traditionally communication is considered to be voice communication, often supported by video. However, it is understood that communication can occur in many forms. It is understood that communication can occur with voice alone, or by text, with alternative media, a robot or similar device, with the assistance of sensors, actuators, or through specialized communications techniques for example, symbols, Braille or similar tactile means, specialized methods including speech to text to graphically generated sign language, through a relay operator or person acting in that capacity, captioning, or sign language on a video display.

It is also understood that a TDD system can be used; TDD systems are also known as teletypewriter, TTY, textphone, and minicom, MCM, Def-tone, DTS, each of these terms are used interchangeably herein.

Communication can also be through touch. This is particularly useful for some protected people for whom traditional communication by voice or text is intimidating. In one configuration software allows a person to select an image using a touch screen menu to convey thoughts or emotions. The image may be directly communicated to the recipient it may also be converted to another form of communication including voice or text. For instance, a protected person might hear their daughter's voice and select a smiley face image, or another emotional image or media to convey a sentiment or message, on the touch screen. Upon that the selection of that image, the device can be configured to say to the daughter, "I am safe and happy." In some embodiments this voice is a computer-generated voice. In other embodiments, the voice is pre-recorded by the protected person. In still other embodiments, the device is configured to synthesize a voice to sound like the protected person having derived the protected person's voice from collected recordings.

Electronic Means

By the term "electronic means" it is meant end to end wired, wireless, radio transmission, and others, inclusive of campus environments such as a closed system (i.e. hospitals), including specialized means such as inductive coupling (e.g. methods of data transfer between implanted medical devices and external systems), near field communications in devices of close proximity (NFC), optical, infrared, scanners, acoustic transmission of data gathered by microphones, and many other means and methods in use to enable connectivity for devices and services. The field of networking is experiencing tremendous growth and diversification, with useful implementations for all aspects of connectivity including traditional wired and wireless communications infrastructure, with additions for simple and secure networking as well as self-configuring ad hoc networking. Over time, some are more abundant and preferred in a given environment such as a medical environment, while others are prevalent because of simplicity, cost, size, safety, embedded infrastructure, practical nature of the method of transmission, etc. Some come with regulatory issues (such as medical devices), others are compliant with standards including Wi-Fi and Bluetooth, and others. Some are more ideally integrated into solutions because of the requirements of the application associated with the power supply, environmental interference issues, and more. The present invention advantages not only the existing internet worldwide communication infrastructure, wired and wireless, as well as campus systems typically found at hospitals, schools, in homes, and elsewhere, but also includes device to device communication, and newly emerging techniques and enablements as needed.

Electronically Cluttered Environment

There are many situations when multiple devices and data transmission techniques are in the same location creating an electronically cluttered environment. This situation can easily occur in a medical setting, rehabilitation situation, assisted living, campuses, schools, and the like. Compounding the situation, in some medical environments, for example, there might be rooms and areas that are inaccessible to wireless communication, or where the wireless communication is blocked. In addition, many wireless communications methods are not designed for cluttered environments affecting the data transmission and causing poor performance or failure of the applications and features. In these and other circumstances, electronic means of communication may advantage alternative methods. Other methods might include but are not limited to, acoustic data transmitted over the air to a receiver such as a microphone or specialized sensor, or a single microphone with a reflective surface to re-create three dimensional sound information for direction, and other information, etc. Devices that may be used with the invention include, but are not limited to, IR or optical sensor collecting data from a display, LED, IR transmitter, screen, etc. The system accounts for short distance, mid-range, and long distance communications through a variety of methods, and anticipates and accommodates for a variety of issues associated with each type of communication.

Protected Person

The devices and methods described herein assist and/or allow for communication between two or more people, wherein one person is a protected person. By protected person is it meant a person who is being cared for by another person, wherein the other person is actively making important decisions for the protected person. For the purpose of this disclosure, the protected person is relying on another person to make decisions, at a minimum, about the other people the protected person communicates with and when that communication is allowed to be conducted.

In some situations, the protected person is of diminished capacity. In some situations, a physician, hospital or clinic has determined that the person lacks capacity to make decisions. In some situations, a court has determined that the person's mental functions are diminished or impaired. In some situations, the court determination is statutory; for instance, a parent or guardian has legal control for their child or ward, at least until the protected person is of legal age. In many situations, the protected person has knowingly volunteered to defer control of their communication to another person for any one of a variety of personal reasons. The status of the protected person may be either permanent or temporary.

Administrative Person

The devices and methods described herein assist and/or allow for communication between two or more people, wherein that communication has been authorized by one or more authorized person. The authorized person is a person who has been entrusted with determining the people with whom the protected person is allowed to communicate. Optionally, the administrative person(s) may determine the times when communication is possible or the maximum duration of communication.

The authorized person is empowered to make decisions for the protected person. At a minimum, the authorized person is empowered to control the communication of the protected person. The authorized person may be empowered by the courts either by an order or by a statutory relationship. For instance, the authorized person could be the parent or guardian of a child, the courts recognize the statutory right of a parent to control the communications of their child. Similarly, the authorized person may be empowered by a doctor or hospital to make decisions on behalf of a protected person. Naturally, the protected person being of sound mind may voluntarily request that the authorized person take control of with whom they communicate.

The authorized person exercises their authority by instructing the device the person with whom the protected person is allowed to communicate; these people are referred to herein as trusted persons. The device does not need for the authorized person to be present for the communication to proceed. The authorized person does not need to know that communication is taking place. The authorized person identifies one or more trusted persons to the device. When communication is initiated from a person the device verifies that the communication is from a trusted person before allowed the communication to proceed with the protected person.

Optionally, the authorized person can provide times when communication is either allowed or prevented. Any time-related schedule for communication is permitted by the device. For instance, the authorized person may block communication during evening hours so that the protected person can sleep. Similarly, the authorized person made blocked communication on a particular day of the week. For instance, communication may be blocked for all people on the Sabbath. Such time periods for communication may be specific to an individual trusted person. Any such limited blocking of communication by individuals or by groups is permitted and possible with the use of the devices and methods described herein.

The duration of communication can also be controlled by the authorized person. For instance, certain persons may be blocked from communicating for more than fifteen minutes with a protected person. Also, the total amount of communication that the protected person is allowed to engage in may be limited. For instance, the authorized person may determine that more than four hours of communication can be detrimental to the protected person's health. Therefore, the total amount of communication time may be permitted limited to just four hours per day.

The devices and methods described herein are capable of allowing for more than one authorized person. The device and methods can be configured for many different hierarchies of determining authorization when more than one authorized person is involved. For instance, it may be agreed that unanimity of authorized persons is required for communication to proceed. Alternatively, it may be determined that any authorized person is able to make the decision to allow participation of a trusted person. Also, it may be agreed that a democratic system is best for determining who is a trusted person. In this system, the authorized persons will be surveyed for their opinion on the status of a person. In some democratic systems, a particular authorized person maybe a tiebreaker to determine the outcome when there is not a majority rule. Also, there may be a requirement for more than fifty percent of the authorized persons to agree in order to designate a person a trusted person. The device and methods described herein can be configured for almost any agreed-upon system for determining trusted people when there is a group of authorized persons.

Figure 9:
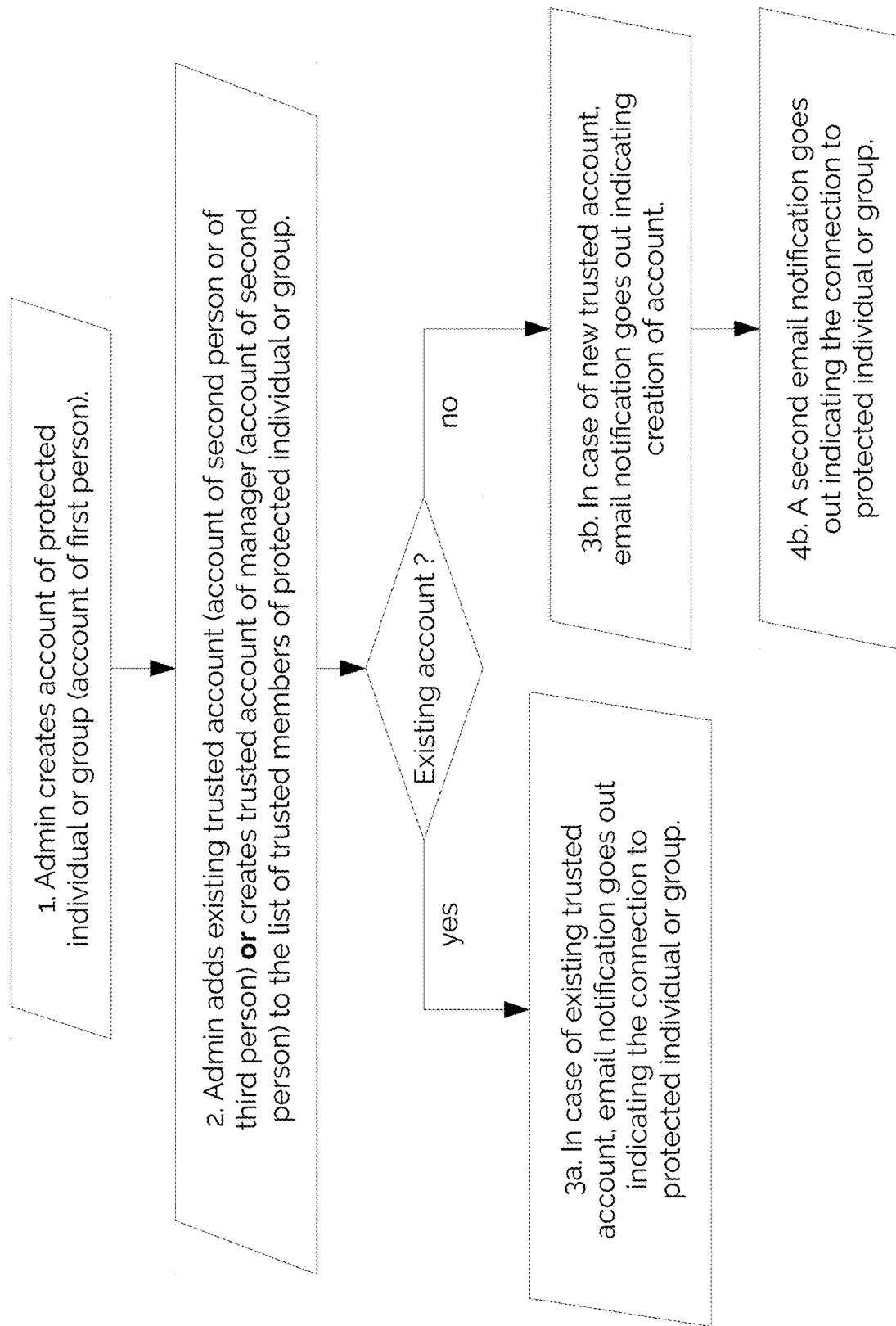
FIG. 9 is a flow chart showing the steps conducted when an administrator is configuring the device for use with a protected person.

It can be readily understood from FIG. 9 the steps conducted when an administrator wished to configure the device for use with a protected person.

Figure 10:
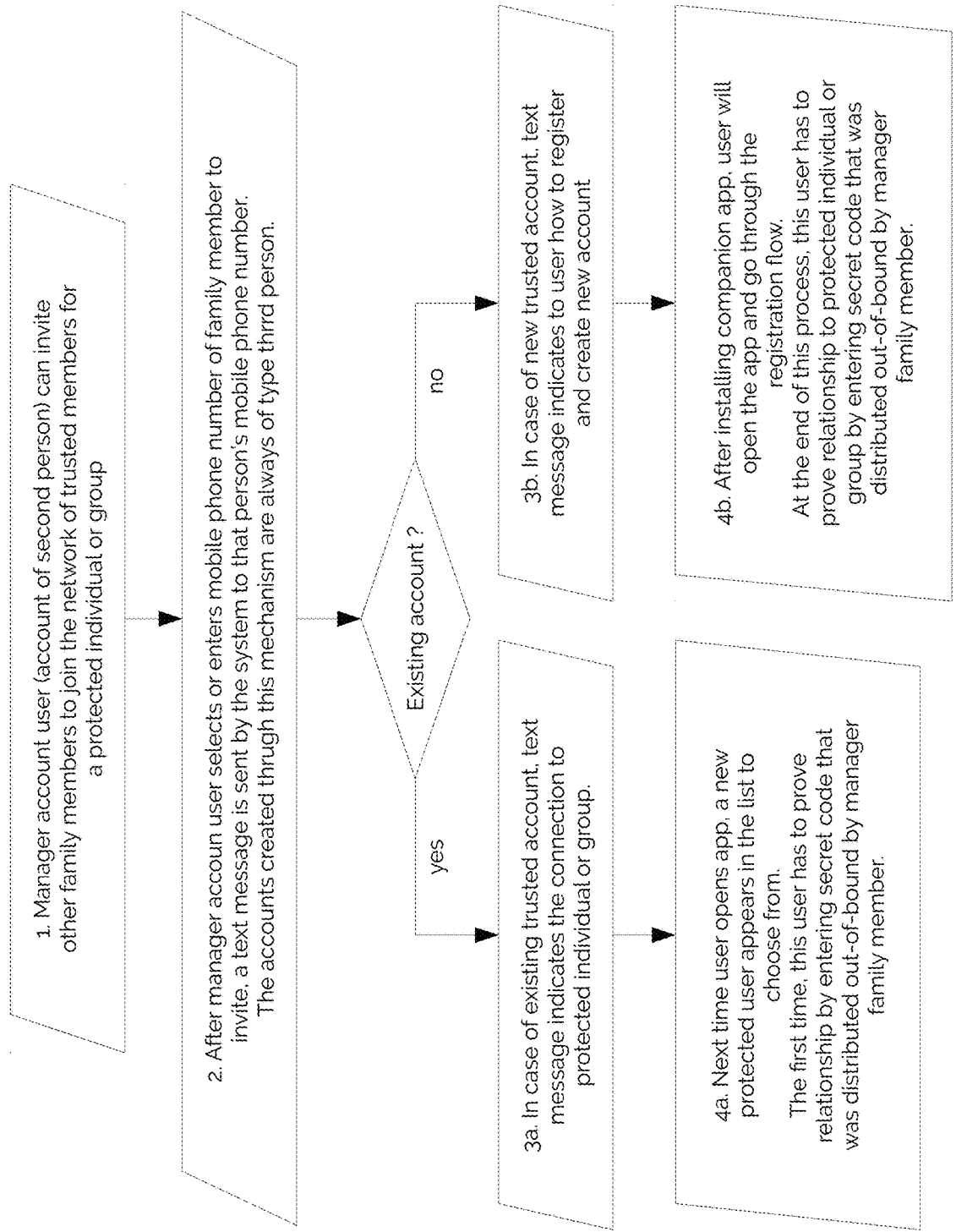
FIG. 10 is a flow chart showing the steps conducted when an administrator creating a group of trusted persons.

It can be readily understood from FIG. 10 the steps conducted when an administrator desires to create a group of trusted persons.

Trusted Person

A trusted person is any person who authorized person, or group of authorized persons, has determined is acceptable to communicate with the protected person. The trusted status of an individual is revocable at the discretion of the authorized person, or group of authorized persons. The trusted status may also be limited by duration, time of day, day of the week, date, or any other factor that is determined to be necessary by the authorized person, or group of authorized persons. Authorization may even be limited to the location of the trusted person. By using the GPS information, IP address or any other location determining data, the device can temporarily withdraw the trusted status based on location. For instance, a grand-daughter may be permitted to communicate with a protected person but not when she is in the home of a not trusted person.

The character of the voice of the communicator can be a factor for temporarily withdrawing trusted status. The authorized person may empower the device to detect harsh tones in a conversation and permit the device to end the communication if harsh tones are detected. Likewise, the device can be configured to detect slurred speech. The device may be enabled to end communication with trusted person when slurred speech is detected. Likewise, offensive or triggering words can be detected by the device and used as a criterion for ending communication. For instance the device can be enabled to block communication when the name of a deceased loved one is mentioned.

The devices and methods described herein can determine the identity of a communicator by a variety of methods to determine if they are a trusted person. Such identifying mechanisms include the ID of the device being used to communicate, the location from which the communication is originating, the voice signature of the person who is communicating and a password given by the person attempting to communicate. A combination of these mechanisms and other conceivable factors can be used in determining the identity of a communicator and verifying that that person is a trusted person.

Pin

It is recognized that there may be reasons when trusted status should and can be conferred to another person. In these situations, one mechanism for transferring trusted status is the use of a PIN, or personal identification number, or another code or identifier used for security, or as a unique identification, that may be assigned using a security system, or an administrator, or might be a biological measure such as a fingerprint, retina scan, voice, word, or another means, for example. For instance it may be necessary or convenient to allow a nurse, for example, to communicate with the protected person however the identity of the nurse on duty at the time may be not known; therefore, the methods and devices described herein can be configured to recognize a PIN as conveying trusted status to an unknown person by recognizing that person as a trusted person.

Pervasive Presence

The methods and devices described herein can be configured so that the device is always active and alert in the presence of the protected person. The device can be configured to recognize the presence of the protected person in the vicinity of the device. Likewise, the device can be configured to recognize the lack of the protected person in the vicinity of the device.

The pervasive presence monitors the protected person, other people, sensors, environment, system applications, responses, communications, schedule, and more to determine when to trigger additional functionality and features, and to maintain an ongoing assessment of the condition of the protected person, circumstances, and more, conduct analysis, determine the state of the protected person, the system and potential actions to be taken, and engage the action or actions, to conduct oversight, reporting, and exception functions. There are a variety of sensors and monitors connected to the dedicated device as elements of the pervasive presence including one or more cameras, for one or more purposes integral to the pervasive presence such as facial recognition, measuring distances, integral to directing rehabilitation, monitoring people, objects, activities including rehabilitation and activities of daily living, gathering data, to measure stride and or gait, locate persons and or objects in the environment, monitor rehabilitation activities, sensors attached to the body to monitor vital signs and compute heart rate variability, one or more microphones to detect voice, sounds, locations of sound-emitting elements, to gather data transmitted by the system elements, connections to the network, to detect interference, efficiency, and impact of electronic connections on performance of the pervasive presence and system, etc. The pervasive presence bridges the gap between sensors in the environment, state of the protected person, state of the system, and prescribed interventions, as well as, and importantly, social interventions to maintain a high-quality life experience for the protected person in a simple, immediate, and automatic manner. The pervasive presence in this invention is also useful to provide data and information for analysis, objective data, subjective data, vital signs measures, medical records, journals, logs of calls, statistics including extent of social network, frequency, duration of calls, number of contacts, nature of communications, etc. to infer the state of the protected person, trusted persons, and to assist in formulating action plans and or interventions to be engaged through notifications, connections, prescriptions, additional social activities, etc.

EXAMPLES

The present invention is further defined in the following Examples. It should be understood that these Examples while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Example 1

In a recent situation using the invention, the protected person who is a lady who speaks only Polish fell ill while visiting her family in an English speaking country, on the east coast of the United States, requiring her to reside in a rehabilitation facility where she was not able to communicate with anyone else in the community including her professional caregivers. This was a very distressing situation for her, for her family, and also for her professional caregivers. Her son, her trusted person, was thousands of miles away in California. By virtue of this invention, he was able to administer a very secure set of services and activities, and the invention was configured as a companion to reduce the burden of technology complexity. He was able to use the system's secure video visits to communicate with his mother on a regular basis, keeping her company and interacting with the professional caregivers. In this manner, he was able to use the system to provide his mother with the companionship of her family. In addition, he was able to virtually visit with the professional caregivers, learning about their plan and his mother's progress in rehabilitation. He was able to translate information for his mother, so she could communicate and learn from the professional caregivers. Since the invention provides a connection that is a pervasive presence and automatic, which is an important aspect of the invention, the son was able to visit with his mother frequently. From his mother's point of view, and because within the security of the system her son was a trusted person, he just appeared on the screen. The protected person, the mother, didn't need to push any button in order to see her son and talk with him. This reduced cognitive burden and complexity for him and for her. The device became a companion for her, and she was no longer alone. The steps involved with a high technology experience were greatly simplified, managed by the invention, addressing her specific needs and abilities, and the anxiety of interacting with a sophisticated high technology communications system was eliminated for the lady.

Example 2

In another implementation of the invention, a senior citizen with dementia residing in an assisted living home was simply not able to use a jitterbug or flip phone. The interface did not meet his needs, and posed a significant cognitive burden preventing him from reaching out to those he loved. He was unable to plan and then to initiate the multiple steps required to engage with the phone, such as to search through a text-based contact list, locate a telephone number stored in the phone, and then initiate a telephone call. However, with the present invention, he became a protected person on a secure system with a customized interface meeting his special needs, which included reducing cognitive burden, providing a specialized interface, and enabling picture touch video calling. The gentleman is now able to communicate with her daughter, a trusted person, through secure video visits that he can initiate himself on the special dedicated screen by touching an image of her daughter's face. Once he touches the screen, the system launches a video call, and his daughter just appears on the screen in one step without any perceived effort on the part of the protected person. The complexity of the task has been significantly reduced to meet the needs of the individual, given the skills he has, and the device becomes a companion to the protected person. The present invention settings have been configured to provide easy access for the protected person to image video calling. Language and reading are complex processes for this protected person, and therefore, the invention enables pictures to be used for accessing and initiating a communication or other process, feature, or function. The video visits provided much-needed support and information to him and to his family whereas he would have been isolated and unable to interact at all with others. In particular, he would have been helpless. He would have been unable to act autonomously, he would have been completely unable to initiate contact, unable to reach out on her own to contact her loved ones. The system was extremely simple for him and his family to use which reduced stress and complexity in the use of technology.

Example 3

In another use of the invention, a lady in Florida who was experiencing mobility issues—difficulty walking, and reduced vision, had difficulty leaving the house. At that point, it became too much for her to continue with her usual activities. In addition, she was also struggling with technology solutions that might have benefited others, to the point where she was even unable to use the telephone. Complicating the situation, her family was located at a great distance, and they resided in a number of other countries and so she was socially isolated. Then she became a protected person, and this invention, with the secure pervasive companion system, enabled her to reach out to her family in a simple manner, meeting her special needs for initiating the connection. The interface was configured to match her specific skills and needs. The secure system enabled her trusted persons, her family, to reach her from all the various locations where they reside. Now her administrative person, a family member, has enabled her trusted persons, members of her family, to connect easily with her from anywhere in the world. She gets updates regularly from the family, including pictures and information about the new babies, even from as far away as Israel. She is no longer so far away. She is happily connected with those she loves.

Example 4

In another ideal use of the invention, a lady who resides in an assisted living facility was having difficulty remembering that there were interesting activities going on right in her facility. She had problems with her memory, and she was not getting out nor interacting very much with others. She became isolated. With the invention however, she receives reminders and alerts informing her of the activities happening in the assisted living facility, many of which are activities in which she shows interest. With the invention, she receives notifications about these interesting activities, right on her device, automatically, and without her having to search or inquire. She is promoted automatically, reminding her when to prepare and go to the activities. As a result, she has shown an increased level of participation which occurred only with the use of this invention. In addition to increased participation, she is keeping her connection with her community, which is essential to maintaining quality of life, reducing risk for depression and anxiety, and which encourages her to participate in exercise, keeping her engaged with others. Importantly, she doesn't have to rely on her own memory, or abilities with technology, or record-keeping, or reviewing calendars on her own, in order to find the activities, prepare, and attend. She has many occasions to look forward to, engaging her socially, keeping her fit, and she is able to prepare and attend the activities without stressful interactions with complex technologies.

Example 5

In another use of the invention, a trusted person, who is a daughter of a protected person is able to send alerts to her mother and to advantage the automatic reminders of the system. She is able to personalize the messages to her mother; in this way, she is able to put a human touch on the reminders in the system as any loved one would like, and this draws the two closer together even though they are far apart. The daughter is able to remind her mother to be careful when leaving the house and to provide a number of personalized and helpful reminders; she is able to let her mother know when it is raining, and that she should prepare by taking her umbrella and raincoat, which is very helpful to her mother and provides a means for the closeness of family. The daughter also personalizes the routine reminders and alerts including medications notifications and activities such as exercise. In this way, the customization of the system becomes a very personalized companion, bringing the loved ones close together in everyday activities which is important for quality of life, companionship, and a sense of social connection. The system enables a customized dialog with guidance by the trusted person and acknowledgments, regular wellness checks through the dialog and through all the activities of daily living, an important measure of wellness.

Example 6

Another implementation of this system addresses the needs of seniors who have health challenges that may lead to disorientation and anxiety. A protected person, who is a senior with health issues, was becoming disoriented and anxious. Through the device, an interface was configured and the administrative person, a daughter, was able to provide a pervasive presence, to display dates and times of important events, with images and familiar pictures. In this manner, the protected person was able to remain more oriented to date, time, events, and important people in his life, thereby reducing anxiety and improving orientation. This was achieved by bringing the protected person a sense of familiarity through the pictures and the trusted person's regular video visits. When a person is in a healthcare or rehabilitation facility, the environment might be somewhat disconnected from cues of the environment including day, time, location, seasons, and more. People can become so disconnected that it impacts their sense of well-being. They can become isolated not only from people but from places and their regular perception of the world. They can be far from the views and perspectives they hold dear. Reminders of routine real-world status such as time, date, and weather were presented visually to improve orientation for this and other protected persons to improve the sense of well-being and connection to the world they enjoy.

Example 7

Knowledge is power, and this invention connects people with people, places, and things in a simple and instant way with pervasive presence. Not everyone experiences their illness or infirmity at the same time. However, there are many common experiences people share and a bit of knowledge can reduce anxiety and improve the protected person's ability to act on their own behalf. With the use of the pictures and videos, the pervasive presence of the protected system organizes content through trusted providers to improve health literacy, personal care for the protected person and their trusted persons, adapted to the needs of the individual and conditions of importance. In addition to connecting with trusted providers, gateways, libraries, and existing resources, the invention provides unique original content to educate protected persons and seniors with chronic conditions and to schedule updates on information about their personal health and prevention, updates to learn best practices and care for their conditions and prevention, questions to detect issues and what to look for and notifications, nutrition and how to eat healthy, and fitness, rehabilitation, and the exercises that they should do, and more. These models of disease management can be updated and expanded and are customizable.

Example 8

The important features of this invention provide a means to engage protected persons in easy connections to reduce isolation and loneliness known to lead to depression, anxiety, and poor outcomes. In addition, the ideal implementation of the system coordinates healthful activities with social connections. Therefore, it is an important aspect of the invention to provide for socialization and exercise, linked through the pervasive companion device with an easy to use customized interface. The invention incorporates live streaming of exercise classes and related education for the protected person to watch on the device at home or in their rooms at residencies. Since the streaming exercise classes are attended by live instructors and other participants, there is an easy connection to social engagement with others. All of this is provided in a secure connection, and without risk of revealing personal information with unknown service providers or others.

Example 9

In one use of the invention, the device is configured to display photos of the trusted person with whom the protected person is speaking. The device is configured to recognize the trusted person by comparing the telephone number of the connected device to a database of information of the trusted persons. Similarly, other information of the connected device can also be used to identify the trusted person. In this example, the photos displayed start in order with the earliest photographs from as closest to the time of the start of the relationship between the trusted person and the protected person. Photographs are displayed in sequence in an order depending on usefulness to the protected person, or, for example, from the earliest to the most recent, for example, or in another order, etc. This age progression is effective in grounding the memory of the trusted person to the present appearance of the trusted person. Often some protected persons have trouble recognizing a current photograph of a loved one but can readily identify the same loved one in an older photograph. The device displaying an age progression of photographs is a tool to assist protected person who has difficulty recognizing the current appearance of their loved ones.

Example 10

Typically, a bar code scanner would be used to scan the patient's identification band, and then scan the medicine drawer to open the drawer, then the medicine label would be scanned to verify the medicine and the patient are matched. However, as we can see in the present invention, use of the camera, which is an integral part of the system, can extend the usefulness of the camera beyond merely observing a scene. For example, by integrating an image recognition system, the patient, the medication or any other object in the scene can be identified automatically. One can see how the present invention uses an architecture of electronic connectivity, and its flexibility, to enable features important to the usefulness of the invention, and to extend usefulness to new techniques and technologies through hardware, standards, software, and oversight by the invention's server. Electronic connectivity on all scales and levels facilitates the smooth interactions that represent the pervasive presence; in fact, that electronic connectivity is integral to the social connections, and is key to the decision making brought to the situation of the protected person, by the present invention in order to determine the state of the protected person, the state from among many potential states of the system, to create and process the recommendations, and to deliver and engage the actions to be taken. There are many known methods of transferring data that are integrated into the invention, and updates to include newly emerging methods are enabled easily by virtue of the invention, as may be seen in the Figures.

Example 11

Figure 11:
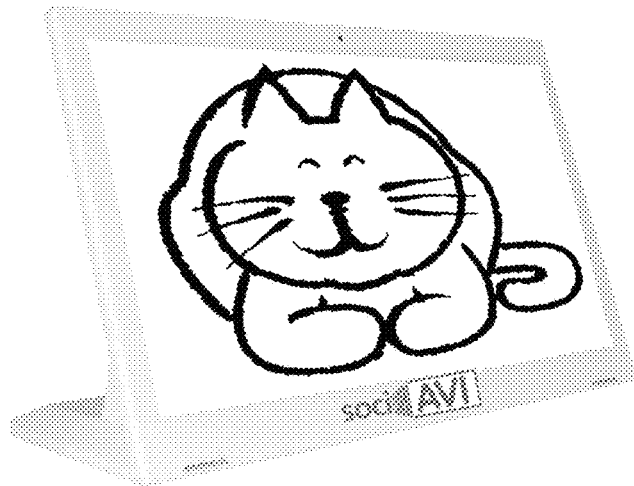
FIG. 11 is an illustration of the device showing an example of emotionally reflective companion feature.

The ideal embodiment of this invention involves determining the state and mood of the protected person and providing appropriate and supplemental social engagements to improve emotional experiences. The system characterizes emotional states and responds to them in a variety of ways. Thus, the pervasive presence is actively providing stimulation to ensure the protected person is not at risk for depression, anxiety, and other sentiments that might impair quality of life. The display might optimally illustrate a happy face, or a smile, or a pet, or photograph of a pleasant reminiscence, or a sound that evokes happiness, etc, see FIG. 11. The display might reflect the sum and analysis of objective and subjective measures, for example, heart rate variability, or image analysis of protected person's semblance, and depending on the assessment, then the pervasive presence initiates an appropriate activity, for example, scheduling social outings, virtual visits, reports to the administrator, and or others, to provide uplifting social experiences. In some cases, displaying pictures and inspirational messages might be useful to elicit a positive response from the protected person; in others, different mechanisms may need to be used. Based on the captured measurements, the most effective intervention for the particular individual will be employed, on an adaptive interface. Through these and other methods, the pervasive presence evolves into a companion for the protected person, and at times takes on an embodied identity through the displays, sounds, media, and other mechanisms.

Example 12

This example shows a general design principle for user interface on dedicated device application. The below description refers FIG. 2 and FIG. 3. FIG. 2 presents an elegant view of the general design principle, whereas FIG. 3 presents a technical presentation.

The Design Principle of the User Interface for the Dedicated Device Application 120 running on the First Device 102 is to overlay screens with different functionality. These screens appear automatically and are usually associated with the message sent, for instance, a photo or video or video visit, to mention a few, or the screen is retrieved through touching the screen in a specific location. There is no use of pinch, zoom, scroll or swipe, or use of menus to navigate or use of keyboard.

The default screen is the Main Screen 160 with the calendar, weather and time. The Picture Slide Show 161 is presented on top of it, and it appears when there is no interaction with the device. When a video comes a new overlay appears on top like Playing Static Video 162, or a Video Visit 163 and subsequently, any new feature would appear as a new overlay 163 that is presented automatically or by the touch of a visible button or a voice-activated command.

We claim:

1. A method of communication between persons comprising a communication between at least two entities;
wherein there is a first person, there is at least one second person and there is at least one third person;
wherein the communication is between the first person and at least one third person;
Wherein the first person has a unique identity;
And wherein the first person's unique identity can be verified by at least one known identifiable characteristic
Wherein all second persons each have a unique identity; and wherein all second persons' identities are different from the first person's identity;
Wherein all third persons each have a unique identity and wherein all third persons' identities are different from the first person's identity;
Wherein at least one second person knows the identity of a third person and has granted approval for that third person to participate in communicating with the first person prior to the initiation of communication with the first person;
Wherein communication is conducted by the first person to the third person through a first device that is coupled to a second device by electronic means
Wherein the first device is electronically coupled to at least one sensor capable of identifying the unique identity of the first person by recognizing at least one physical characteristic of the first person by electronic means and
Wherein the first device is always active and connected electronically to a server when it is in the presence of the first person.

2. The method of claim 1, wherein the first device comprises a microphone capable of transducing sound;
Wherein the first device comprises a speaker capable of transmitting sound; and,
Wherein the communication between the first person and the third person is vocal.

3. The method of claim 1, wherein the first device comprises a camera capable of transducing images;
Wherein the first device comprises a display capable of displaying transmitted images; and,
wherein the communication between the first person and the third person is video.

4. The method of claim 1, wherein the first device comprises a touch-sensitive display capable of displaying images and transducing touch; and
wherein the communication between the first person and the third person through the first person touching the touch-sensitive display.

5. The method of claim 1, wherein the first person is a child.

6. The method of claim 1, wherein the first person is a person over the age of 65.

7. The method of claim 1, wherein the first person is a person who has been legally determined to be incompetent.

8. The method of claim 1, wherein the first person is a person who has been medically determined to have diminished mental functions.

9. The method of claim 1, wherein the device is configured to recognize a PIN as a code transmitted by the second person as confirmation that the second person has granted approval for the third person to communicate with the first person.

10. The method of claim 9, wherein the second person has entered a PIN into the second device to be transmitted the first device.

11. The method of claim 1, wherein the sensor capable of identifying the unique identity of the first person by recognizing at least one physical characteristic of the first person by electronic means is a digital camera.

12. The method of claim 11, wherein the camera is capturing infrared light.

13. The method of claim 1, wherein the sensor capable of identifying the unique identity of the first person by recognizing at least one physical characteristic of the first person by electronic means is a microphone.

\* \* \* \* \*